United States Patent
Oag et al.

(10) Patent No.: US 11,768,387 B2
(45) Date of Patent: Sep. 26, 2023

(54) TUNEABLE OPHTHALMIC LENS

(71) Applicant: CooperVision International Limited, Fareham (GB)

(72) Inventors: Robert Oag, Southampton (GB); Ian Bruce, Southampton (GB); Robin Frith, Southampton (GB); Percy Lazon de la Jara, San Ramon, CA (US); Rachel Marullo, Oakland, CA (US)

(73) Assignee: COOPERVISION INTERNATIONAL LIMITED, Fareham (GB)

( * ) Notice: Subject to any disclaimer, the term of this patent is extended or adjusted under 35 U.S.C. 154(b) by 0 days.

(21) Appl. No.: 17/770,642

(22) PCT Filed: Oct. 14, 2020

(86) PCT No.: PCT/GB2020/052579
§ 371 (c)(1),
(2) Date: Apr. 21, 2022

(87) PCT Pub. No.: WO2021/079093
PCT Pub. Date: Apr. 29, 2021

(65) Prior Publication Data
US 2022/0413321 A1 Dec. 29, 2022

Related U.S. Application Data

(60) Provisional application No. 62/925,815, filed on Oct. 25, 2019.

(51) Int. Cl.
*G02C 7/08* (2006.01)
*G02C 7/04* (2006.01)

(52) U.S. Cl.
CPC .............. *G02C 7/085* (2013.01); *G02C 7/049* (2013.01)

(58) Field of Classification Search
CPC .................................. G02C 7/049; G02C 7/085
(Continued)

(56) References Cited

U.S. PATENT DOCUMENTS 4,174,156 A * 11/1979 Glorieux .................. G02B 3/14
359/666
4,466,705 A * 8/1984 Michelson ............. G09B 23/30
351/159.33
(Continued)

FOREIGN PATENT DOCUMENTS

AU 2015264899 B2 * 3/2017 ............... G02B 3/14
CN 1788224 A * 6/2006 ........... G02B 26/005
(Continued)

OTHER PUBLICATIONS

International Search Report and Written Opinion issued in corresponding International Patent Application No. PCT/GB2020/052579 dated Jan. 14, 2021 (13 pages).
(Continued)

*Primary Examiner* — James R Greece
(74) *Attorney, Agent, or Firm* — Kilyk & Bowersox, P.L.L.C.

(57) ABSTRACT

The present disclosure concerns a tuneable ophthalmic lens 200. The tuneable ophthalmic lens comprises an activated state and a deactivated state. The ophthalmic lens further comprises a central chamber 206b. The ophthalmic lens also comprises a fluid reservoir, the fluid reservoir being in fluid communication with the central chamber. The fluid reservoir comprises a pump for pumping fluid between the fluid reservoir and the central chamber. In the deactivated state the central chamber is substantially empty of fluid 208a. In the activated state the central chamber is not substantially empty of fluid.

15 Claims, 5 Drawing Sheets

(58) Field of Classification Search
USPC .................................................. 351/159.68
See application file for complete search history.

(56) References Cited

U.S. PATENT DOCUMENTS

| | | | | |
|---|---|---|---|---|
| 4,477,158 | A * | 10/1984 | Pollock | G02B 3/14 |
| | | | | 351/159.04 |
| 4,816,031 | A * | 3/1989 | Pfoff | A61F 2/1648 |
| | | | | 623/6.22 |
| 7,261,736 | B1 * | 8/2007 | Azar | A61F 2/08 |
| | | | | 623/6.22 |
| 2006/0290882 | A1 * | 12/2006 | Meyers | G02C 7/049 |
| | | | | 351/159.62 |
| 2007/0142909 | A1 * | 6/2007 | Peyman | G02B 3/14 |
| | | | | 623/6.11 |
| 2007/0153231 | A1 * | 7/2007 | Iuliano | G02C 7/041 |
| | | | | 351/159.34 |
| 2008/0002149 | A1 * | 1/2008 | Fritsch | G02C 7/049 |
| | | | | 351/159.02 |
| 2008/0231799 | A1 * | 9/2008 | Iuliano | G02C 7/041 |
| | | | | 351/159.18 |
| 2011/0235186 | A1 * | 9/2011 | Blum | G02C 7/08 |
| | | | | 359/665 |
| 2012/0019773 | A1 * | 1/2012 | Blum | G02B 3/14 |
| | | | | 351/159.01 |
| 2012/0038883 | A1 * | 2/2012 | Peyman | A61F 2/1635 |
| | | | | 351/159.07 |
| 2012/0092775 | A1 * | 4/2012 | Duston | G02B 3/14 |
| | | | | 359/666 |
| 2013/0242255 | A1 * | 9/2013 | Caldarise | G02C 7/049 |
| | | | | 351/159.36 |
| 2014/0232982 | A1 * | 8/2014 | Iwai | G02C 7/085 |
| | | | | 351/159.03 |
| 2014/0276481 | A1 | 9/2014 | Pugh et al. | |
| 2014/0343387 | A1 * | 11/2014 | Pugh | A61B 5/6821 |
| | | | | 600/365 |
| 2015/0370093 | A1 * | 12/2015 | Waite | B29D 11/00038 |
| | | | | 585/16 |
| 2016/0004098 | A1 * | 1/2016 | Waite | G02C 7/045 |
| | | | | 351/159.14 |

FOREIGN PATENT DOCUMENTS

| | | | | |
|---|---|---|---|---|
| CN | 105962887 | A * | 9/2016 | |
| CN | 106999167 | A * | 8/2017 | ......... A61B 10/0045 |
| WO | WO-2005096026 | A2 * | 10/2005 | .......... G02B 26/005 |
| WO | WO-2007142602 | A1 * | 12/2007 | ............... G02B 3/14 |
| WO | 2012051167 | A1 | 4/2012 | |
| WO | WO-2012051167 | A1 * | 4/2012 | ............... G02B 3/14 |
| WO | 2012061411 | A1 | 5/2012 | |
| WO | WO-2012061411 | A1 * | 5/2012 | .......... A61F 2/1624 |
| WO | 2015191247 | A1 | 12/2015 | |
| WO | WO-2016135434 | A1 * | 9/2016 | .......... G02F 1/1334 |
| WO | 2016173620 | A1 | 11/2016 | |
| WO | WO-2016174181 | A2 * | 11/2016 | .......... A61F 2/1635 |
| WO | 2017060537 | A2 | 4/2017 | |
| WO | WO-2017060537 | A2 * | 4/2017 | .......... A61F 2/1635 |
| WO | 2019122435 | A2 | 6/2019 | |

OTHER PUBLICATIONS

Second Written Opinion issued in corresponding International Patent Application No. PCT/GB2020/052579 dated Sep. 28, 2021 (7 pages).

International Preliminary Report On Patentability issued in corresponding International Patent Application No. PCT/GB2020/052579 dated Mar. 1, 2022 (with Article 34 claims) (13 pages).

* cited by examiner

TUNEABLE OPHTHALMIC LENS

This application is a National Stage Application of PCT/GB2020/052579, filed Oct. 14, 2020, which claims priority to U.S. Provisional Application No. 62/925,815, filed Oct. 25, 2019.

FIELD OF THE PRESENT DISCLOSURE

The present disclosure concerns tuneable ophthalmic lenses. The present disclosure also concerns a method of tuning an ophthalmic lens.

Background of the Present Disclosure

A significant number of people suffer from vision defects, for example myopia (short sightedness) or hyperopia (long sightedness). As these people get older, they may develop presbyopia (where the lens becomes less elastic, which makes it more difficult for the eye to accommodate, i.e. to increase its focusing power in order to focus on near objects). A common way of correcting the vision in this situation is the use of varifocal or bifocal eyeglasses. These glasses have a different focal length near the top of the lens compared with the bottom of the lens; however, this means that vision through part of the lens is always out of focus depending on the activity of the wearer, and as such many people opt for two separate pairs of glasses: one for near sight and one for far sight. Else, the wearer has to angle their eyes or their head in order to use the different parts of the lens. This is cumbersome. Multifocal contact lenses or bifocal contact lenses have also been developed in an effort to help presbyobes see clearly at near viewing distances and far viewing distances.

Conventional ophthalmic lenses are set at a specific power that is determined when the ophthalmic lens is manufactured, and as such are often unable to remedy the above issue by themselves. Some alternative conventional ophthalmic lenses have been designed to overcome this problem. One way is for each contact lens of a contact lens pair having a different power. For example, the contact lens in the left eye might have a refractive power for distance vision, and the contact lens in the right eye might have a refractive power for near vision. This is termed 'monovision' as the wearer of this type of contact lens system no longer has binocular vision, which can be problematic. Another alternative design is to have a contact lens with a central optical zone that encompasses parts of the contact lens with different powers. For example, the centre of the central optical zone might have a refractive power for near vision, and a ring shaped region around the centre (still within the central optical zone) may have a refractive power for distance vision. This produces two images on the retina, and the neural optical pathways of the wearer are required to select which image to 'look' at. Some variants of this have more than one zone of each power. Many wearers complain of problems including ghosting when using contact lenses of this variety. It would therefore be desirable to have an ophthalmic lens that is capable of adjusting its power, not only for near and far sight, but also for when the strength of correction required by the eye changes with time.

Ophthalmic lenses have been proposed that have a central chamber that is filled with fluid. WO 2019/122435 discloses a contact lens with a central chamber that is supplied with fluid from adjacent fluid reservoirs. As the lens volume is filled with fluid, the lens changes shape and therefore changes its focal length/power. One of the problems associated with the prior art is that when there is a loss of power, the base power of the lens is also lost and can leave the wearer with blurred vision in both the near and far distance.

An example contact lens of the prior art will now be described with reference to FIGS. 1a and 1b. FIGS. 1a and 1b show a cross-sectional side view of contact lens 100.

In FIG. 1a, contact lens 100 comprises two main layers: first lens portion 102; and second lens portion 104. In the centre of contact lens 100, there is central chamber 106, which is arranged to be positioned over the pupil of the eye of the wearer of contact lens 100. In central chamber 106, between first lens portion 102 and second lens portion 104, there is provided fluid cavity 108, which is filled with fluid 108a. Contact lens 100 is also provided with fluid reservoir(s) (not shown) that are in fluid communication with fluid cavity 108. More fluid 108a can be transported from the fluid reservoir(s) to fluid cavity 108, thus inflating fluid cavity 108 and making central chamber 106 more convex in shape. This is shown in FIG. 1b. This increases the power of the lens, enabling the wearer to view objects relatively close to the eye.

One of the problems associated with the lenses of the prior art is that the volume of fluid to be maintained in fluid cavity 108 in the 'base power' state (FIG. 1a) is very precise and accurate. This is difficult to achieve consistently with every transition to and from the inflated state of FIG. 1a, and small variations in the volume of fluid in fluid cavity 108 can change the focal length/power of central chamber 108 in a significant enough manner to be detectable by the wearer. Furthermore, should there be a loss of power to contact lens 100, the 'base power' of the lens is also lost and can leave the wearer with blurred vision in both the near and the far distance.

The present disclosure seeks to mitigate the above-mentioned problems. Alternatively or additionally, the present disclosure seeks to provide an improved tuneable ophthalmic lens.

SUMMARY OF THE PRESENT DISCLOSURE

The present disclosure provides, according to a first aspect, a tuneable ophthalmic lens as claimed in claim 1.

According to a second aspect of the present disclosure, there is also provided a method of tuning an ophthalmic lens as claimed in claim 11.

According to a third aspect of the present disclosure, there is also provided a method of manufacturing a tuneable ophthalmic lens as claimed in claim 12.

According to a fourth aspect of the present disclosure, there is also provided a kit of parts as claimed in claim 15.

Optional but preferred features are set out in the dependent claims.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present disclosure will now be described by way of example only with reference to the accompanying schematic drawings.

DETAILED DESCRIPTION

Figure 1A:
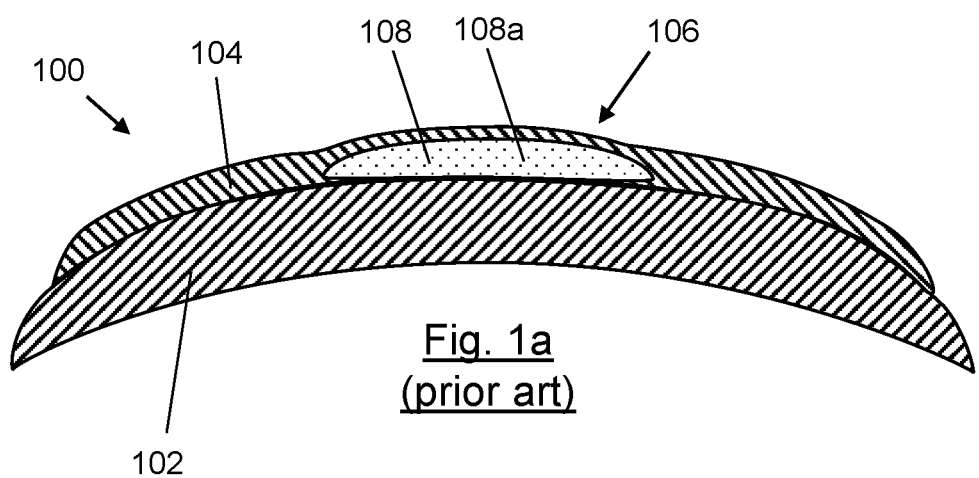
FIG. 1a shows a cross-sectional side view of a contact lens in a deactivated state according to the prior art.
Figure 1B:
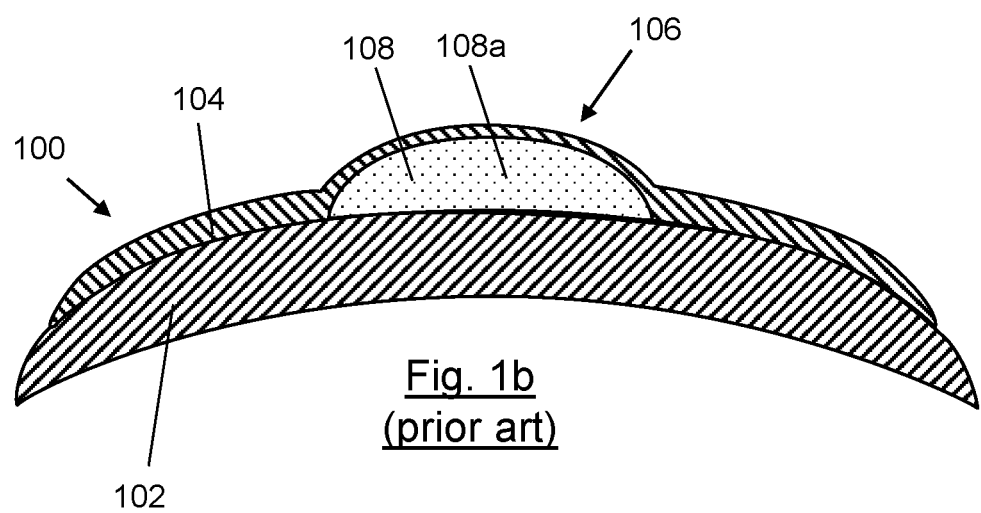
FIG. 1B shows a cross-sectional side view of the contact lens of FIG. 1a in an activated state according to the prior art.

The present disclosure will be more fully understood and further advantages will become apparent when reference is made to the following detailed description of embodiments of the present disclosure, wherein like reference numerals denote similar elements.

In the following description, the terms "first lens portion" and "second lens portion" refer to portions that form part of an ophthalmic lens. Optionally, first lens portion is not a lens, i.e. the power of first lens portion may be substantially zero. Optionally, second lens portion is not a lens, i.e. the power of second lens portion may be substantially zero. When specifically in reference to contact lenses, the first lens portion refers to the portion that makes up the contact lens that is in contact with an eye when the contact lens is in use. The second lens portion, when in reference to contact lenses, refers to the portion, which makes up the contact lens, which forms part of the external curvature of the contact lens, when the contact lens is in use on an eye.

As set out above, the first aspect of this disclosure provides according to a first aspect, a tuneable ophthalmic lens. The tuneable ophthalmic lens comprises an activated state and a deactivated state. The ophthalmic lens further comprises a central chamber. The ophthalmic lens also comprises a fluid reservoir. The fluid reservoir is in fluid communication with the central chamber. The ophthalmic lens further comprises a pumping mechanism for pumping fluid from the fluid reservoir to the central chamber. The pumping mechanism is a pump. The ophthalmic lens is configured to have an activated state, in which the pump has pumped fluid into the central chamber. The ophthalmic lens is also configured to have a deactivated state, in which the central chamber is substantially empty of fluid or completely empty of fluid.

The central chamber is configured to be inflated with fluid. The boundary of the central chamber is defined by a circumferential wall, and an external surface. The external surface faces away from an eye, when the ophthalmic lens is in use. The external surface also forms part of the second lens portion. The central chamber may also be enclosed by a portion of a surface of the first lens portion. The fluid for inflating the central chamber is supplied by the fluid reservoir. The pumping mechanism pumps the fluid between the reservoir and the central chamber when required. Advantageously, there is no requirement to move the head of the wearer to fill/empty the central chamber of fluid. When the wearer needs to correct their near vision (to be able to see nearby objects), the ophthalmic lens is activated and the central chamber is pumped with fluid from the fluid reservoir. This causes the ophthalmic lens, and more specifically the central chamber to inflate. This, in turn, causes the central optical zone, to become more convex, and hence increases the optical power of the lens. The pump may be arranged to pump fluid from the central chamber to the fluid reservoir. To then correct for distance vision (to be able to see more distant objects), the fluid may either be pumped out of the central chamber, or the fluid may be allowed to flow out of the central chamber. This causes the central chamber to have a more 'flat' external surface, thus causing the ophthalmic lens and central optical zone to become more concave (i.e. less convex), and hence decreasing the optical power of the lens. The central optical zone refers to the region of the ophthalmic lens that is configured to be positioned over the pupil of an eye when in use. The central optical zone may encompass a portion of the central chamber. The central optical zone may encompass the entirety of the central chamber. The central optical zone may encompass the entirety of the central chamber, and a further portion of the second lens portion.

If power to the ophthalmic lens—and more specifically the pumping mechanism—is lost, then the central chamber deflates and reverts to the deactivated state. In the deactivated state, the focal length/power of the ophthalmic lens may be determined by the curvature and refractive index of the second lens portion, which is determined when the ophthalmic lens is manufactured. The first lens portion may have substantially no focal power. The power of the contact lens in the deactivated state may be determined by the curvature and refractive index of the first lens portion. The power of the contact lens in the deactivated state may be determined by the curvature and refractive index of both the first and second lens portions. Advantageously, when power is lost and the ophthalmic lens reverts back to the deactivated state, the ophthalmic lens becomes more concave (less convex). If the ophthalmic lens were to lose power, the wearer would still be able to see long distance. This is particularly advantageous for driving, for example, as it is beneficial for the wearer to be able to see long distance in these situations.

It may be that the central chamber is not 100% empty of fluid in the deactivated state: a small, known volume of fluid may remain in the central chamber in the deactivated state. The volume of fluid in the central chamber may be less than 10% of the total volume of fluid in the ophthalmic lens, when in the deactivated state. The volume of fluid in the central chamber may be less than 5% of the total volume of fluid in the ophthalmic lens, when in the deactivated state. The volume of fluid in the central chamber in the deactivated state may be less than 4%, or 3%, or 2%, or 1% of the total volume of fluid in the ophthalmic lens. There may be substantially no fluid in the central chamber when the ophthalmic lens is in the deactivate state. Substantially no fluid may be regarded as a volume of less than 0.5% of the total volume of fluid in the ophthalmic lens.

When transitioning to the activated state, the change in focal length/strength of the central chamber may be as a result of the change in shape of the lens.

The first lens portion may comprise or consist of silicone hydrogel. The second lens portion may comprise or consist of silicone hydrogel. Alternately, the first lens portion may comprise or consist of a silicone elastomer material. Similarly, the second lens portion may comprise or consist of a silicone elastomer material. In some embodiments, the first lens portion and the second lens portion comprise or consist of a silicone elastomer material.

The pump may be an osmotic pump. Osmotic pumps have low power consumption, and also can finely control the volume passing through the osmotic membrane.

The central chamber is not substantially empty of fluid when in the activated state. The volume of fluid in the central chamber may be between 10% and 100% of the total volume of fluid in the ophthalmic lens, when the ophthalmic lens is in the activated state. The volume of fluid in the central chamber may be between 5% and 95% of the total volume of fluid in the ophthalmic lens, when the ophthalmic lens is in the activated state. The upper bound of this range may account for some fluid remaining in the pumping mechanism, when in the activated state. The volume range present in the central chamber when in the activated state may represent the volume of fluid needed to change the shape of the central optical zone to have a noticeable effect on the vision of the wearer.

The volume of fluid in the central chamber, when the ophthalmic lens is in the activated state, may be continuously variable. In such embodiments, the volume of fluid in the central chamber may be fine-tuned, or by extension the focal length/power of the central chamber may be fine-tuned. Therefore, the focal length/power of the central chamber may be continuously variable. This has the advantage that the volume of fluid in the central chamber, when the ophthalmic lens is in the activated state, is not limited by discrete changes in volume and can be adjusted to small changes/variations of the wearer's eye with time.

The volume of fluid in the central chamber may be controlled external to the ophthalmic lens. The pumping mechanism may comprise a wireless communication module. The wireless communication module may communicate with a control module. The control module may be external to the ophthalmic lens. The control module may be configured to receive an input from the wearer of the ophthalmic lens. The control module may be configured to receive an input from a person wanting to adjust the focal length/power of the ophthalmic lens. The input may be a manual input. The control module may communicate the input wirelessly to the pumping mechanism, via the wireless communication module. The control module may receive an input, and convert the input into an instruction. The instruction may be communicated wirelessly to the pumping mechanism. The wireless communication to the pumping mechanism may be via a wireless communication module connected to the pumping mechanism. The instruction may comprise a voltage to be applied to the pumping mechanism. The instruction may comprise a required volume of fluid to be maintained in the central chamber. The instruction may comprise an indication of the volume of fluid to be present in the central chamber. The instruction may be interpreted by the wireless communication module, or the pumping mechanism, and converted into a voltage output. The instruction may comprise switching the ophthalmic lens to the deactivated state. The instruction comprising switching the ophthalmic lens to the deactivated state may comprise setting the voltage output to the pumping mechanism to zero.

The ophthalmic lens may be a contact lens. Optionally, the ophthalmic lens may be an intraocular lens.

The central chamber may be biased towards the deactivated state. The central chamber may comprise an elastic external surface, whereby the central chamber is biased towards the deactivated state. The external surface of the central chamber may be elastically deformed in the activated state. This has the advantage that when the ophthalmic lens is in the activated state, the fluid in the central chamber is under pressure from the central chamber. When the pump has power, the volume of fluid in the central chamber is maintained. When power is lost to the pump, the force of the external surface of the central chamber on the fluid inside the central chamber causes the fluid to vacate the central chamber via channels to the fluid reservoir. Under circumstances where the pump has power, the fluid may be pumped out of the central chamber. The fluid may passively vacate the central chamber. The fluid may passively vacate the central chamber under normal operating conditions, for example when the pump has power. The pump may be used to inflate the central chamber, and may be used to maintain a specified volume of fluid in the central chamber, while the biasing of the central chamber causes fluid to passively vacate the central chamber. The biasing of the central chamber towards the deactivated state acts as a failsafe, as when in the deactivated state, the ophthalmic lens is configured for distance vision, which is especially beneficial for a wearer who is wearing the ophthalmic lens while driving, for example.

As set out above, the second aspect of the present disclosure provides a method of tuning an ophthalmic lens. The ophthalmic lens comprises a central chamber and a fluid reservoir. The fluid reservoir is in fluid communication with the central chamber. The method comprises the step of pumping fluid from the fluid reservoir to the central chamber. The fluid is pumped such that the ophthalmic lens transitions from a deactivated state, to an activated state. In the deactivated state, the central chamber is substantially empty of fluid. In the activated state, the pump has pumped fluid into the central chamber.

The ophthalmic lens may be calibrated such that a known amount of fluid is required to be pumped into/out of the central chamber to change the focal length/strength of the central chamber by a predetermined amount.

As set out above, the third aspect of the present disclosure provides a method of manufacturing an ophthalmic lens of the first aspect of the present disclosure. The method comprises the step of forming a first lens portion. The method further comprises the step of forming a second lens portion. The method also comprises forming a central chamber and a fluid reservoir. The fluid reservoir is in fluid communication with the central chamber. The method comprises the step of positioning a pumping mechanism to be in fluid communication with the fluid reservoir. The pumping mechanism is a pump. The method also comprises bonding the first lens portion to the second lens portion, to form the tuneable ophthalmic lens.

The skilled person will appreciate that the order of the steps presented is not necessarily the order in which they are to be performed, and is not intended to limit the scope of the claims to the order presented in the claims. For example, the steps of forming the second lens portion, and forming the central chamber and fluid reservoir, may be performed before the step of forming the first lens portion.

The method may comprise forming a recess in the first and/or second lens portion. The recess may form the fluid reservoir. According to embodiments of the present disclosure, the central chamber and/or the fluid reservoir may be at least partially filled with fluid prior to the bonding step.

The pump may be an osmotic pump. The pump may be a mechanical pump.

The ophthalmic lens may be a contact lens. The ophthalmic lens may be an intraocular lens.

Figure 2A:
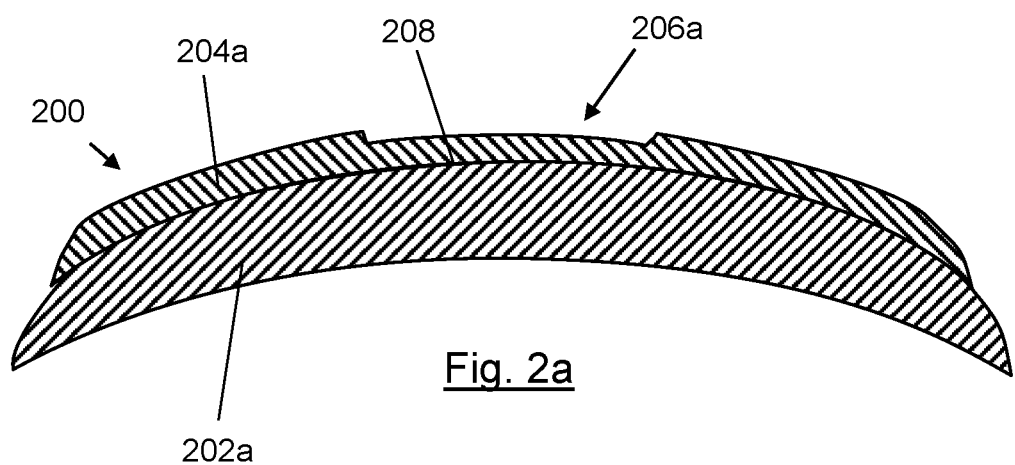
FIG. 2a shows a cross-sectional side view of a tuneable contact lens in a deactivated state according to an embodiment of the present disclosure.

As set out above, the fourth aspect of the present disclosure provides a kit of parts comprising: (a) a tuneable ophthalmic lens as claimed in any of claims 1 to 10, the lens including a communication module; and (b) a control module for communicating with the communication module FIG. 2a shows a cross-sectional side view of contact lens 200 in a deactivated state according to an embodiment of the present disclosure. Contact lens 200 comprises two main layers: first lens portion 202a; and second lens portion 204a. First lens portion 202a and second lens portion 204a are made from a silicone hydrogel material or a silicone elastomer material. In the centre of contact lens 200, there is central chamber 206a, which is arranged to be positioned over the pupil of the eye of the wearer of contact lens 200. In central chamber 206a, between first lens portion 202a and second lens portion 204a, there is provided fluid cavity 208. Fluid cavity 208, in the deactivated state in this embodiment is substantially empty of fluid. Substantially empty of fluid means a volume of fluid within fluid cavity 208 of less than 0.5% of the total volume of fluid in contact lens 200. Therefore, the optical properties of contact lens 200 in the deactivated state are substantially dictated by the refractive index and curvature of first lens portion 202a and second lens portion 204a. Contact lens 200 is also provided with a fluid reservoir (not shown) that is in fluid communication with fluid cavity 208.

In the deactivated state, contact lens 200 has a net concave curvature. In this state, contact lens 200 corrects for short-sightedness, and enables the wearer to see distant objects more clearly.

Figure 2B:
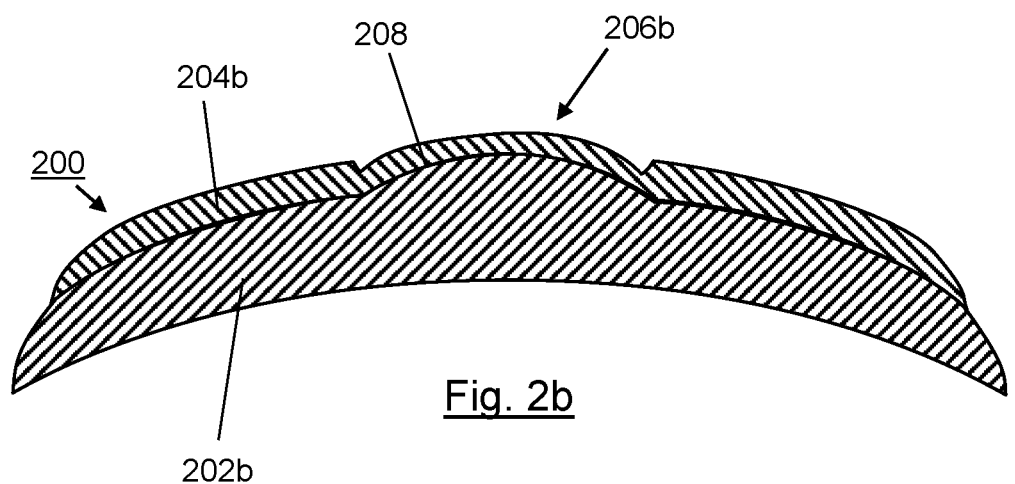
FIG. 2b shows a cross-sectional side view of a tuneable contact lens in a deactivated state according to an embodiment of the present disclosure.
Figure 2C:
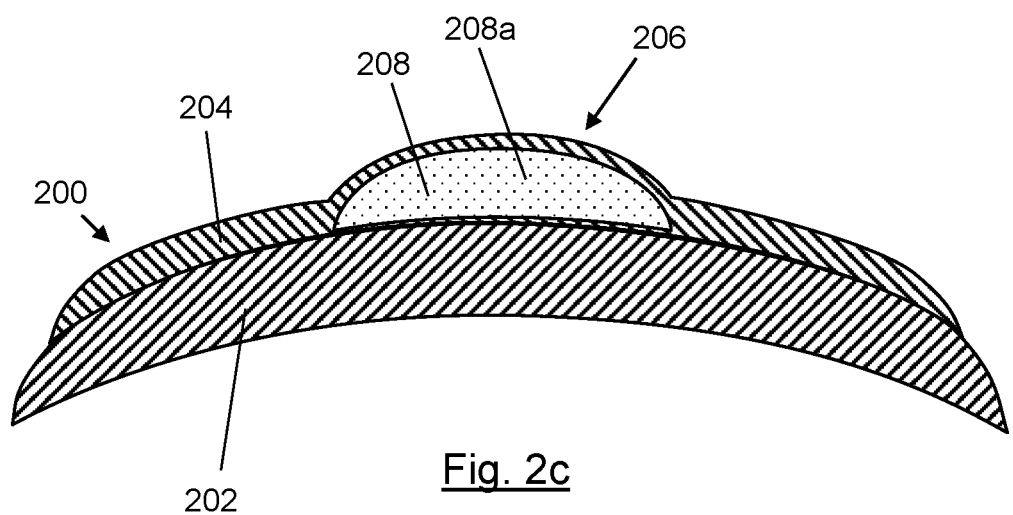
FIG. 2c shows a cross-sectional side view of the tuneable contact lens of FIG. 2a in an activated state.

To provide accommodation, i.e. to correct for near vision, fluid (reference numeral 208a in FIG. 2c) is transported from the fluid reservoir to fluid cavity 208, thus inflating fluid cavity 208 and making central chamber 206a more convex in shape (as shown in FIG. 2c).

The optical properties of contact lens 200 in the deactivated state are determined prior to manufacture, as these optical properties are present when the pump in the fluid reservoir (not shown) is not active. Contact lens 200 is manufactured to a specification, where the base focal length/power of contact lens 200 in the deactivated state matches the prescription for the end user, in order to correct their short-sightedness (or myopia). The base power of contact lens 200 matches the prescription for distance vision. The base power of contact lens 200 refers to the weakest power.

This is shown in the embodiment of FIG. 2b, for example. FIG. 2b shows a cross-sectional side view of contact lens 200 in the deactivated state, according to an embodiment of the present disclosure. The curvature of central chamber 206b is greater than the curvature of central chamber 206a in FIG. 2a. This difference in curvature in the central chamber in the deactivated state is to match different prescriptions for the minimum optical power required of contact lens 200. Both first lens portion 202b and second lens portion 204b have a convex portion in central chamber 206b. Compared to the lens of FIG. 2a, the more convex shape of central chamber 206b will shorten the focal length within the eye more than central chamber 206a, and correct for long-sightedness in comparison to the central chamber 206a of FIG. 2a, which corrects for short-sightedness.

Between first lens portion 202b and second lens portion 204b, in central chamber 206b, there is provided fluid cavity 208. Fluid cavity 208, in the deactivated state in this embodiment of the present disclosure, is substantially empty of fluid. Therefore, as with FIG. 2a, the optical properties of contact lens 200 in the deactivated state are substantially dictated by the refractive index and curvature of first lens portion 202b and second lens portion 204b.

Contact lens 200 is also provided with a fluid reservoir (not shown) that is in fluid communication with fluid cavity 208. The fluid reservoir also includes a pump. In embodiments of the present disclosure, the pump is an osmotic pump.

To provide accommodation, i.e. to correct for near vision—i.e. to shorten the focal length of central chamber 206b—fluid is pumped from the fluid reservoir to fluid cavity 208. This causes fluid cavity 208 to expand and push upwards on second lens portion 204b in central chamber 206b. This changes the curvature of central chamber 206b and causes it to become more convex (see FIG. 2c, for example).

FIG. 2c shows a cross-sectional side view of contact lens 200 in an activated state, according to an embodiment of the present disclosure. In the activated state, fluid cavity 208 has been inflated with fluid 208a. Central chamber 206, in the activated state, has a greater external curvature (i.e. a smaller radius of curvature), in comparison to the deactivated state (such as in the embodiment of FIG. 2a). The only variable factor affecting the focal length/power of central chamber 206 is the curvature of central chamber 206. In the activated state, central chamber 206 is more convex, and as such corrects for near vision.

If power to the pump (not shown) were to be lost, then fluid cavity 208 would empty of fluid and central chamber 206 would revert to the base (manufactured) state. The base state is manufactured to a prescription for the wearer to correct distance vision. Therefore, even if contact lens 200 loses power, the wearer of contact lens 200 is still able to see in the long distance which is particularly advantageous if the wearer was to lose power to their contact lens 200 when driving, for example.

Figure 2D:
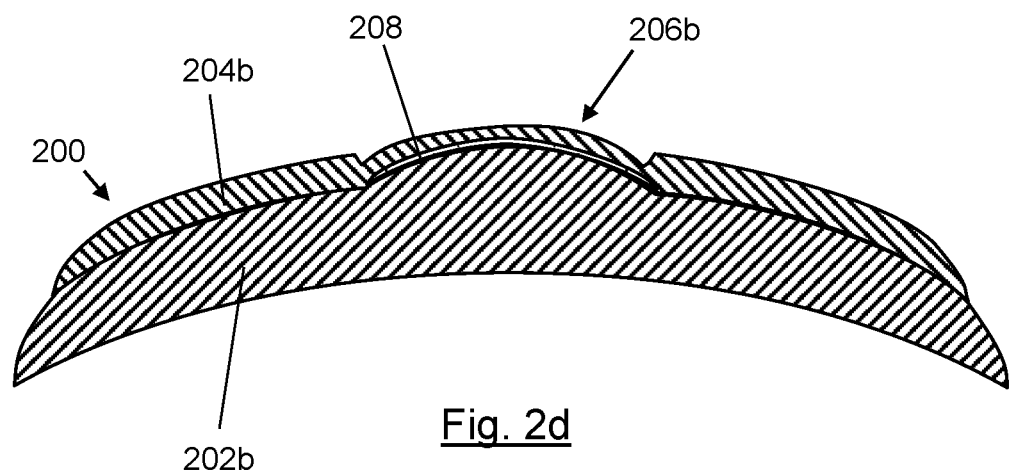
FIG. 2d shows a cross-sectional side view of the tuneable contact lens of FIG. 2b in a deactivated state.

FIG. 2d shows a cross-sectional side view of contact lens 200 in a deactivated state according to an embodiment of the present disclosure, in which the lens 200 corrects for the long-sighted wearer's distance vision. The difference between the embodiment of FIG. 2d and the embodiment of FIG. 2b is that in the deactivated state there is a small amount of fluid left within fluid cavity 208 in the embodiment of FIG. 2d. The amount of fluid within fluid cavity 208 is known and accounted for when contact lens 200 is manufactured such that when contact lens 200 loses power and contact lens 200 reverts to the shown deactivated state, the focal length/power of central chamber 206b is appropriate for the prescription of the wearer of contact lens 200. It may not be physically possible to remove 100% of all the fluid from fluid cavity 208, and as such some fluid may remain. This amount of fluid is determined through testing and manufacture of contact lens 200 and is accounted for when manufacturing contact lens 200 to a specific prescription. The fluid reservoir (not shown) is sized to be able to hold 100% of the fluid contained within contact lens 200, however.

The amount of fluid remaining in the fluid cavity when the ophthalmic lens is in the deactivated state may have negligible effect on the power of the lens, compared to if the fluid cavity (and therefore the central chamber) was completely empty of fluid.

A further advantage of the embodiments herein described is that less fluid is required in contact lens 200, as fluid cavity 208 may transition between being substantially empty of fluid, to containing almost all of the fluid in contact lens 200. This is different from the prior art, which has a significant amount of fluid in the fluid cavity at the 'smallest volume' setting.

Figure 3:
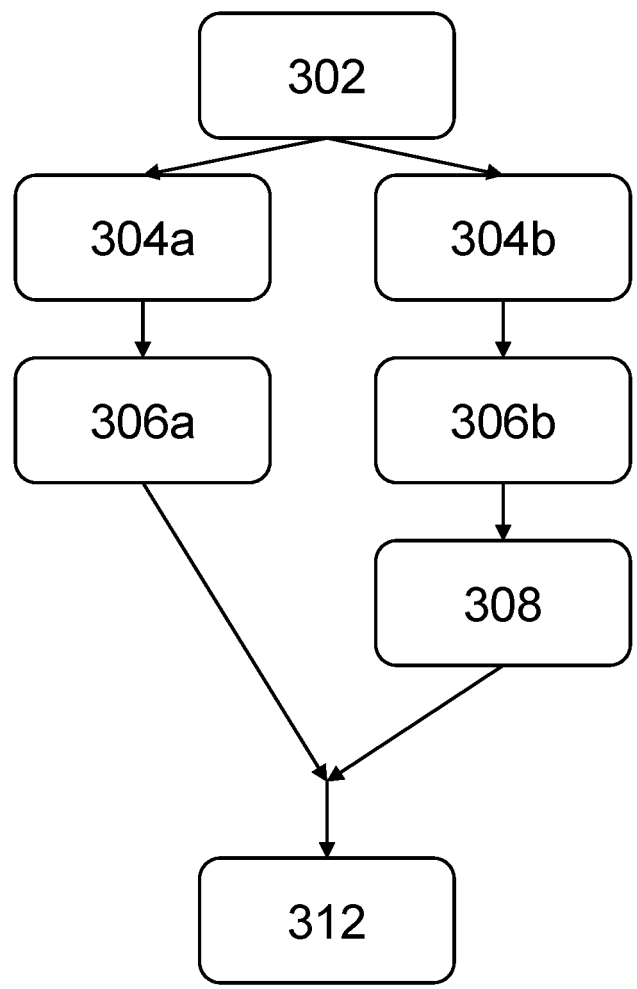
FIG. 3 shows a flowchart of a method of manufacturing an ophthalmic lens according to an embodiment of the present disclosure.

The following is an exemplary method of manufacture of a tuneable contact lens, according to an embodiment of the present disclosure. FIG. 3 shows a flowchart of a method of manufacturing an ophthalmic lens according to an embodiment of the present disclosure.

The method comprises the step of forming a first lens portion. The first lens portion is formed of a silicone hydrogel material or a silicone elastomer material. The first lens portion is formed in a lens portion molding assembly, which comprises a first mold part and a second mold part assembled together. The first and second mold parts are formed in mold part forming step 302. Mold part forming 302 uses metal dies. A surface of each of a pair of metal dies corresponds to a surface of a mold part to be formed. Considering that only one surface of the mold part to be formed is used in the formation of any of the contact lens components, the die used to form the other surface does not need to form a particular shape. One of the dies may be flat, for example. The other die may have a concave cavity. This forms a mold part with a convex anterior surface and a flat rear surface. Mold part forming 302 includes holding the dies together and injection molding a first mold part. A similar second pair of dies are used to form a second mold part, also by injection molding. The second pair of dies may include a die with a convex protrusion, while the second die of the second pair may be flat. The first die of the second pair may have a convex protrusion with a flat top, such that an eventual first lens portion comprises a flat top in the region of the central chamber. The mold part formed in this second pair of dies would therefore have a concave surface and a flat (rear) surface.

Mold part forming step 302 also includes the formation of a pair of injection molded molds that are used to form a second lens portion. The injection molded molds for forming the second lens portion may be a different shape to the molds for forming the first lens portion. The method steps for forming the pair of molds for forming the second lens portion are substantially the same as the steps for forming the pair of molds for forming the first lens portion.

In this example, the die forming the concave surface includes recesses that lead to the formation of recesses in the second lens portion, the recesses corresponding to the central region, the fluid reservoir, and channels therebetween.

A dry first lens portion is then formed in first lens portion forming step 304a. A dry second lens portion is also then formed in step 304b. The steps for the formation of both of these lens portions is substantially the same and is as follows. In the case of hydrogel members or silicone hydrogel members, the first lens portion (or second lens portion) can be made by polymerizing a hydrogel or silicone hydrogel lens formulation that includes a polymerization initiator in a first lens portion shaped cavity formed between the first mold part and the second mold part. For silicone elastomer members, the first lens portion can be made by curing, vulcanizing, or catalyzing, such as by hydrolysation, a liquid silicone elastomer material in a first lens portion shaped cavity formed between the first mold part and the second mold part. The surface of each mold part that forms the lens member shaped cavity may be convex, concave, planar or a combination of thereof. After formation of the first lens portion, the two mold parts are separated such that the first lens portion remains attached to the surface of one of the mold parts. As a result, a first lens portion is provided on a surface of the first or second mold part. In embodiments of the present disclosure, it is desirable to place the first lens portion on a surface of a mold part that was not used to produce the first lens portion, but that may require additional steps to achieve the desired alignment of the member to the mold part.

Washing steps 306a and 306b involve washing of the first lens portion and the second lens portion respectively. Any residue from the formation of the first lens portion and the second lens portion in the mold parts is washed off. Also in this step, the washing causes the dry lens portions to swell as water is retained within the membrane of the lens portions.

In a recess enhancing step 308, the second lens portion is held in a receptacle. A recess enhancing surface of a predetermined shape is then pressed into the concave side of the second lens portion to plastically deform the recess in the second lens portion that will go on to form the fluid reservoir. This process is known as pre-stressing the second lens portion. The result of this is that the second lens portion undergoes permanent strain. A second recess forming arm may be pressed into the concave side of the second lens portion to further plastically deform further recesses in the second lens portion that will go on to form further fluid reservoirs. The fluid reservoir comprises a pumping mechanism. The pumping mechanism is a pump. The fluid reservoir and the central chamber may be formed in one formation step, as opposed to two separate formation steps followed by a connections step.

The method further comprises bonding step 312. Bonding step 312 is the step of bonding the bulk lens to the second lens portion, to form a tuneable contact lens. As mentioned earlier in the description, the "second lens portion" includes the central chamber, and the fluid reservoir.

The first lens portion or second lens portion is provided on a compliant stage. The compliant stage may have a greater flexibility than the first and/or second mold parts. The provision of the first lens portion or the second lens portion on the compliant stage can be done manually, or it can be done using an automated machine, such as a robotic device. Optionally, each of the first lens portion and/or second lens portion is provided on a compliant stage.

The compliant stage provided as a support for the first lens portion and/or second lens portion may be of a material that is more pliable than the material of the first mold part and/or second mold part. Using a deformable material to form the compliant stage facilitates ensuring proper alignment and sufficient bonding of the second lens portion to the first lens portion. For example, the contact between the second lens portion and the first lens portion is more complete than when the first lens portion is provided on a rigid convex surface.

The second lens portion is provided on a concave surface. Fluid is then dispensed onto the concave side of the second lens portion such that it sits within the recesses formed in recess forming step 308. Fluid is dispensed onto the fluid reservoir such that it is filled. Optionally, fluid is not be dispensed onto the central chamber. This is to ensure that when the contact lens is eventually formed, it is known to be possible to evacuate all of the fluid from the central chamber. In embodiments of the present disclosure, fluid may be dispensed into the central chamber and not the fluid reservoir. In embodiments of the present disclosure, fluid may be dispensed into both the central chamber and the fluid reservoir such that they are both only partially filled with fluid.

The first lens portion located on the compliant stage is placed in contact with the second lens portion. The first lens portion may be provided on a rigid mold part, or on a compliant stage. The placement of the first lens portion on the second lens portion is such that the second lens portion is aligned with the first lens portion, and the compliant stage/stages provides compression to the second lens portion and/or first lens portion.

Once the second lens portion and the first lens portion are in contact, the methods of the present disclosure then include a step of joining the second lens portion and the first lens portion to form the tuneable contact lens. The joining can be achieved using an adhesive, or curing the components together, and the like. This joining step of the method may include one or more of the following steps:

Modifying a surface of the first lens portion and or second lens portion, for example prior to bringing the first lens portion and second lens portion into contact;

Bonding the second lens portion to the first lens portion, for example by heating the second lens portion and the first lens portion while they are in contact;

Clamping the second lens portion and the first lens portion while they are in contact, for example before bonding;

According to embodiments of the present disclosure, the methods include a step of modifying a surface, e.g. a concave surface, of the second lens portion and/or modifying a surface, e.g. a convex surface, of the first lens portion by exposing the second lens portion and/or the first lens portion respectively to a plasma treatment process. In other words, the surfaces of the second lens portion and first lens portion can be activated by exposing them to plasma.

Figure 4:
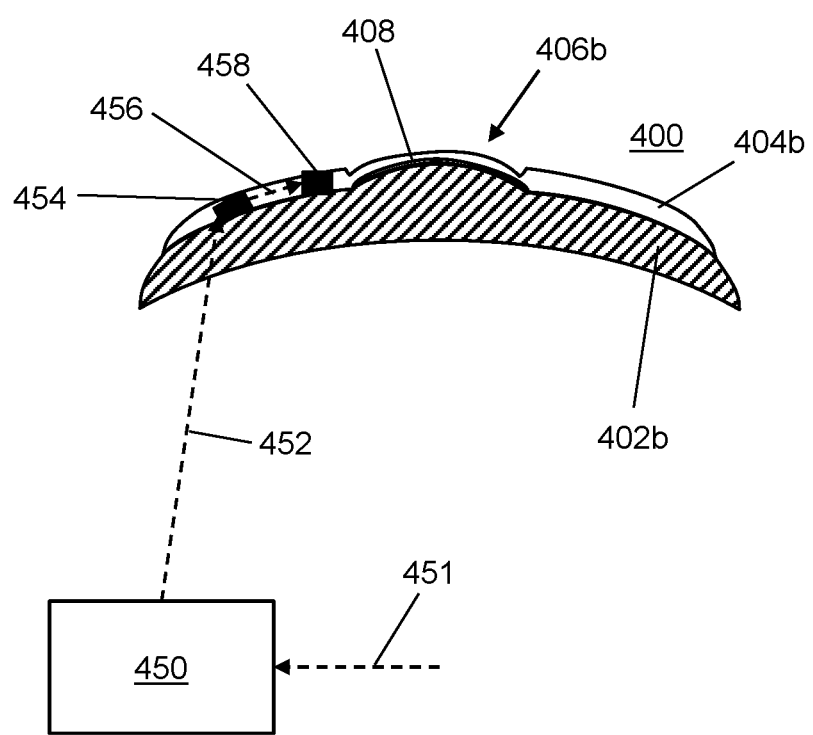
FIG. 4 shows a schematic diagram of a method of tuning an ophthalmic lens according to an embodiment of the present disclosure.

In the embodiment of FIG. 4, the ophthalmic lens is a contact lens. Contact lens 400 is similar in structure to contact lens 200 of FIG. 2d (the hatching has been removed from second lens portion 404b to more clearly see the additional details). Contact lens 400 is in the deactivated state, in which central chamber 406b is substantially empty of fluid. Contact lens 400 comprises a pump 458. Pump 458 includes a wireless communication module 454. Wireless communication module 454 communicates pump settings 456 to pump 458. There is also provided a control module 450. Control module 450 communicates wirelessly to wireless communication module 454. Control module 450 is configured to receive manual inputs 451 from a wearer of the contact lens. Control module 450 is external to contact lens 400.

Control module 450 may be comprised in a mobile telephone device. The interface by which a wearer of the ophthalmic lens may provide manual inputs may be a software application on a device. Control module 450 may be comprised in a bespoke device designed to house a control module for tuning an ophthalmic lens.

Control module 450 receives manual inputs 451 from the wearer of contact lens 400, and converts the inputs 451 into an instruction 452. Control module 450 communicates instruction 452 to wireless communication module 454. The instruction comprises an indication of the volume of fluid to be present in the central chamber.

The instruction may comprise switching the ophthalmic lens to the activated state. The instruction may comprise switching the ophthalmic lens to the deactivated state. The instruction may comprise an "on" instruction, and an "off" instruction.

Wireless communication module 454 converts instruction 452 to pump setting 456. In the embodiment of FIG. 4, pump setting 456 comprises switching pump 458 on, such that pump 458 pumps fluid into central chamber 406b, and such that contact lens 400 transitions to the activated state.

The control module may comprise a plurality of predetermined instructions. The instructions may be pre-calibrated for the prescription of the wearer of the contact lens. The user input may comprise requesting that the contact lens switch between near vision, and distance vision. There may be other distances that the contact lens is configured to switch between. The user input may comprise requesting that the contact lens switch to medium distance vision, or reading vision, for example. The control module may be pre-calibrated to convert these pre-selected user inputs to instructions. The pump may switch between a plurality of pre-calibrated settings. Each setting may correspond to a distance.

Whilst the present disclosure has been described and illustrated with reference to particular embodiments, it will be appreciated by those of ordinary skill in the art that the present disclosure lends itself to many different variations not specifically illustrated herein. By way of example only, certain possible variations will now be described.

Optionally, the first lens portion is not made of silicone hydrogel material or a silicone elastomer material. Optionally, the second lens portion is not made from silicone hydrogel material or a silicone elastomer material. Optionally, the first lens portion is not formed of the same material as the second lens portion. The material used for either or both layers may be any other suitable lens material, such as hydrogel, or rigid gas permeable lenses made from silicone acrylate or variants of such.

Optionally, the method of manufacture may comprise providing a hydrophobic coating. The hydrophobic coating may be provided on at least part of the concave surface of the second lens portion. The hydrophobic coating may alternatively or additionally be provided on at least part of the convex surface of the first lens portion. The parts of the first and/or second lens portions that are coated with hydrophobic coating may be arranged to form the central region and/or the inflatable ring.

Advantageously, the use of a hydrophobic coating in the regions of the lens where liquid is stored improves the retention of liquid within the lens. Soft contact lenses may transmit water to help to ensure that they do not stick to the eye. The hydrophobic coating can ensure that the liquid contained within the lens does not leave its confinement.

Optionally, the pump is not an osmotic pump, and is an electro-mechanical actuator. The skilled person would readily appreciate which forms of pump may be suitable for the application of the present disclosure.

In the deactivated state, the fluid cavity is substantially empty of fluid (such as in FIG. 2d). In the deactivated state, the volume of fluid in the fluid cavity may represent less than 5% of the total volume of fluid in the contact lens. The volume of fluid in the fluid cavity may represent less than 4% of the total volume of fluid in the contact lens. The volume of fluid in the fluid cavity may represent less than 3%, or may represent less than 2%, or may represent less than 1%, of the total volume of fluid in the contact lens. It may be inevitable that some fluid is left within the fluid cavity when it is in the deactivated state. The fluid left in the fluid cavity when in the deactivated state may form an annular ring within the fluid cavity at its internal circumference.

Optionally, the fluid does not have substantially the same refractive index as the first lens portion, or optionally does not have substantially the same refractive index as the second lens portion, or optionally does not have substantially the same refractive index as either layer. The refractive index of the fluid may be chosen to enhance the refractive properties of the contact lens. Choosing a fluid with a high refractive index may mean that less fluid is required to achieve the same focal length/power as a contact lens that contains a fluid with a lower refractive index. Where the fluid has a refractive index that is different to the lens material, the focal length/power may be determined by a combination of the curvature of the central chamber, and the interaction of the different refractive indices of the fluid and first lens portion and second lens portion.

Optionally, the first lens portion and second lens portion is formed from a single piece of material, such that the contact lens is formed from a single piece of material. The first lens portion and the second lens portion may be formed separately, and then fused together to form a single piece.

The invention claimed is:

1. A tuneable contact lens comprising:
   a first lens portion that is in contact with an eye when the lens is in use; and
   a second lens portion which forms part of an external curvature of the contact lens when the lens is in use, wherein the first and second lens portions are fused together to form a single piece;
   a central chamber between the first lens portion and the second lens portion, wherein a boundary of the central chamber is defined by a circumferential wall and an external surface, the external surface forming part of the second portion and facing away from the eye when the lens is in use, and wherein the central chamber is enclosed by a portion of a surface of the first lens portion;
   a fluid reservoir, the fluid reservoir being in fluid communication with the central chamber; and
   a pump that is voltage activatable and is configured to pump fluid from the fluid reservoir to the central chamber upon application of an applied voltage;
   the lens being configured to have an activated state, in which the pump receives voltage and pumps fluid into the central chamber, and a deactivated state, in which the pump does not receive voltage and the central chamber is substantially empty of fluid, wherein the central chamber is biased towards the deactivated state, and wherein the biasing of the central chamber causes fluid to passively vacate the central chamber, thereby changing the optical power of the lens.

2. The tuneable contact lens of claim 1, wherein the pump is an osmotic pump or a mechanical pump or an electromechanical actuator.

3. The tuneable contact lens of claim 1, wherein the pump comprises a plurality of settings, each setting corresponding to a predetermined volume of fluid in the central chamber.

4. The tuneable contact lens of claim 1, wherein a volume of fluid in the central chamber is continuously variable.

5. The tuneable contact lens of claim 1, wherein when in the deactivated state the central chamber contains less than 3 percent of the total volume of fluid in the contact lens.

6. The tuneable contact lens of claim 1, wherein when in the activated state the central chamber contains between 10 percent and 95 percent of the total volume of fluid in the contact lens.

7. The tuneable contact lens of claim 1, wherein the pump includes a wireless communication module.

8. The tuneable contact lens as claimed in claim 7, wherein the wireless communication module is configured to communicate wirelessly to a control module.

9. The tuneable contact lens of claim 1, wherein the pump is arranged to pump fluid from the central chamber to the fluid reservoir.

10. The tuneable contact lens of claim 1, wherein the central chamber comprises an elastic external surface, whereby the central chamber is biased towards the deactivated state.

11. A method of tuning a tuneable contact lens, the contact lens comprising: a first lens portion that is in contact with an eye when the lens is in use and a second portion which forms part of an external curvature of the contact lens when the lens is in use, wherein the first and second lens portions are fused together to form a single piece; a central chamber between the first and second lens portions, wherein a boundary of the central chamber is defined by a circumferential wall and an external surface, the external surface forming part of the second portion and facing away from the eye when the lens is in use, and wherein the central chamber is enclosed by a portion of a surface of the first lens portion, ands a fluid reservoir, the fluid reservoir being in fluid communication with the central chamber; and a pump that is voltage activatable, the method comprising the step of:
   pumping fluid from the fluid reservoir to the central chamber by applying a voltage to the pump, whereby the contact lens transitions from a deactivated state, in which the central chamber is substantially empty of fluid, to an activated state, in which the pump has pumped fluid into the central chamber, wherein the central chamber is biased towards the deactivated state, and wherein the biasing of the central chamber causes fluid to passively vacate the central chamber, thereby changing the optical power of the lens.

12. A method of manufacturing the tuneable contact lens of claim 1, the method comprising the steps of:
   forming the first lens portion;
   forming the second lens portion,
   forming the central chamber, the central chamber being biased towards the deactivated state, and a fluid reservoir in the first and/or second lens portion, the fluid reservoir being in fluid communication with the central chamber;
   positioning a pump to be in fluid communication with the fluid reservoir; and
   bonding the first lens portion to the second lens portion, to form the tuneable contact lens.

13. The method of claim 12, wherein the central chamber and/or the fluid reservoir is at least partially filled with fluid prior to the bonding step.

14. The method of claim 11, wherein the pump is an osmotic pump.

15. A kit of parts comprising:
   (a) the tuneable contact lens of claim 1, the lens including a communication module; and
   (b) a control module for communicating with the communication module.

* * * * *